(12) United States Patent
Teverovskiy et al.

(10) Patent No.: US 10,590,072 B2
(45) Date of Patent: Mar. 17, 2020

(54) PARTIALLY FLUORINATED AROMATIC ESTERS

(71) Applicant: 3M INNOVATIVE PROPERTIES COMPANY, St. Paul, MN (US)

(72) Inventors: Georgiy Teverovskiy, St. Louis Park, MN (US); Chetan P. Jariwala, Woodbury, MN (US); Thomas P. Klun, Lakeland, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/317,105

(22) PCT Filed: Aug. 29, 2017

(86) PCT No.: PCT/US2017/049082
§ 371 (c)(1),
(2) Date: Jan. 11, 2019

(87) PCT Pub. No.: WO2018/048675
PCT Pub. Date: Mar. 15, 2018

(65) Prior Publication Data
US 2019/0241510 A1 Aug. 8, 2019

Related U.S. Application Data

(60) Provisional application No. 62/385,457, filed on Sep. 9, 2016.

(51) Int. Cl.
| | | |
|---|---|---|
| *C07C 311/09* | (2006.01) | |
| *C08K 5/435* | (2006.01) | |
| *C08K 5/17* | (2006.01) | |
| *C08L 75/04* | (2006.01) | |

(52) U.S. Cl.
CPC ............ *C07C 311/09* (2013.01); *C08K 5/175* (2013.01); *C08K 5/435* (2013.01); *C08L 75/04* (2013.01)

(58) Field of Classification Search
CPC ........ C07C 311/09; C08K 5/435; C08L 75/04
See application file for complete search history.

(56) References Cited

U.S. PATENT DOCUMENTS

| | | |
|---|---|---|
| 3,971,373 A | 7/1976 | Braun |
| 4,100,324 A | 7/1978 | Anderson |
| RE30,782 E | 10/1981 | van Turnhout |
| 4,375,718 A | 3/1983 | Wadsworth |
| RE31,285 E | 6/1983 | van Turnhout |
| 4,429,001 A | 1/1984 | Kolpin |
| 4,588,537 A | 5/1986 | Klasse |
| 4,592,815 A | 6/1986 | Nakao |
| 4,619,976 A | 10/1986 | Morris |
| 4,843,134 A | 6/1989 | Kotnour |
| 5,025,052 A | 6/1991 | Crater |
| 5,145,727 A | 9/1992 | Potts |
| 5,149,576 A | 9/1992 | Potts |
| 5,300,587 A | 4/1994 | Macia |
| 5,336,717 A | 8/1994 | Rolando |
| 5,380,778 A | 1/1995 | Buckanin |
| 5,411,576 A | 5/1995 | Jones |
| 5,451,622 A | 9/1995 | Boardman |
| 5,459,188 A * | 10/1995 | Sargent .................... C08K 5/02 524/316 |
| 5,688,884 A | 11/1997 | Baker |
| 5,898,046 A | 4/1999 | Raiford |
| 5,977,390 A | 11/1999 | Raiford |
| 6,114,419 A | 9/2000 | Liss |
| 6,127,485 A * | 10/2000 | Klun .......................... C08J 5/18 525/199 |
| 6,753,380 B2 * | 6/2004 | Qiu ........................ C07C 311/09 428/357 |
| 7,396,866 B2 | 7/2008 | Jariwala |
| 2006/0135673 A1 * | 6/2006 | Temperante ............. C08K 5/10 524/463 |

FOREIGN PATENT DOCUMENTS

| | | | |
|---|---|---|---|
| CN | 102675490 A | * | 9/2012 |
| JP | 58196284 A | * | 11/1983 |
| WO | WO 1997-22576 | | 6/1997 |
| WO | WO 1998-15598 | | 4/1998 |
| WO | WO 1999-05345 | | 2/1999 |
| WO | WO 2016-069674 | | 5/2016 |
| WO | WO 2017-074709 | | 5/2017 |
| WO | WO 2017-100045 | | 6/2017 |
| WO | WO 2017-210006 | | 12/2017 |

OTHER PUBLICATIONS

Derwent Abstract of CN 102675490 A, 2012 (Year: 2012).*
Davies, "The Separation of Airborne Dust and Particles," Institution of Mechanical Engineers, London, Proceedings, 1952, vol. 1B, No. 1-12, pp. 185-198.
Fielding, Organofluorine Compounds and Their Industrial Applications, 214-234, (1979).
Phillips, "Application of ESCA and Contact Angle Measurements to Studies of Surface Activity in a Fluoropolymer Mixture", Journal of Colloid and Interface Science, Aug. 1976, vol. 56, No. 2, pp. 251-254.
Wente, "Manufacture of Super Fine Organic Fibers", Report No. 4364 of the Naval Research Laboratories, May 25, 1954, pp. 1-20.
Wente, "Superfine Thermoplastic Fibers," Industrial Engineering Chemistry, Aug. 1956, vol. 48, No. 8, pp. 1342-1346.
International Search Report for PCT International Application No. PCT/US2017/049082, dated Nov. 27, 2017, 4 pages.

\* cited by examiner

*Primary Examiner* — Nicole M. Buie-Hatcher

(57) ABSTRACT

Described are compounds of the formula: wherein $R^{Aryl}$ is an aryl group; $R^1$ is a linear or branched $C_2$-$C_{40}$ hydrocarbyl group; $R^2$ is a $C_1$-$C_4$ alkyl; $R_f$ is a perfluorinated group of having an average of 3 to 5 carbon atoms; and subscript x is 1 to 3.

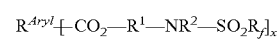

11 Claims, No Drawings

PARTIALLY FLUORINATED AROMATIC ESTERS

CROSS REFERENCE TO RELATED APPLICATIONS

This application is a national stage filing under 35 U.S.C. 371 of PCT/US2017/049082, filed Aug. 29, 2017, which claims the benefit of U.S. Application No. 62/385,457, filed Sep. 9, 2016, the disclosure of which is incorporated by reference in its/their entirety herein.

BACKGROUND

This invention relates to partially fluorinated sulfonamide compounds having fluoroaliphatic and fluorine-free aliphatic groups. This invention also relates to polymer compositions comprising the fluorochemical composition and shaped articles made from the thermoplastic composition.

The utility of organofluorine compounds as surface-active agents (i.e., surfactants) and surface-treating agents is due in large part to the extremely low free-surface energy of a $C_6$-$C_{12}$ fluorocarbon group, according to H. C. Fielding, "Organofluorine Compounds and Their Applications," R. E. Banks, Ed., Society of Chemical Industry at p. 214 (1979). Generally, the organofluorine substances described above are those which have carbon-bonded fluorine in the form of a monovalent fluoroaliphatic radical such as a perfluoroalkyl group, typically —$C_nF_{2n+1}$, where n is at least 3, the terminal part of which group is trifluoromethyl, —$CF_3$.

Several patents have taught that the addition of certain fluorochemicals to thermoplastic imparts oil and stain repellency to thermoplastic articles such as fibers. For example, U.S. Pat. No. 5,025,052 (Crater et al.) describes the use of fluoroaliphatic radical-containing 2-oxazolidinone compounds having a monovalent fluoroaliphatic radical bonded to the 5-position thereof with an organic linking group. The compounds are said to be useful in the surface treatment of fibrous materials, such as textiles and are also useful in preparing fibers, films and molded articles by melt-extrusion or injection molding.

U.S. Pat. No. 5,380,778 (Buckanin) describes the use of fluorochemical aminoalcohols in thermoplastic compositions which can be melted and shaped, for example by extrusion or molding, to provide fibers and films having desirable oil- and water-repellency properties.

U.S. Pat. No. 5,451,622 (Boardman et al.) describes shaped articles, such as fibers and films, made by melt extruding mixtures of fluorochemical piperazine compounds and a thermoplastic polymer.

U.S. Pat. No. 5,898,046 describes repellent compositions formed by the mixture of a thermoplastic polymer and a fluorocarbon/aliphatic hydrocarbon monoester, wherein the aliphatic hydrocarbon portion can have from about 12 to about 76 carbon atoms.

International Published Application WO 97/22576 (Raiford et al.) describes fluorochemical diesters added to thermoplastic polymer melts which impart repellency of low surface tension fluids to the resultant fiber, fabric, nonwoven, film or molded article.

International Published Application WO 99/05345 (Gasper et al.) discloses a hydrophobic and oleophobic fiber comprising synthetic organic polymer and a compound which is a fluorochemical ester or amide derived from a dimer or trimer acid.

U.S. Pat. No. 5,411,576 (Jones et al.) describes an oily mist resistant electret filter media comprising melt-blown electret microfibers and a melt-processible fluorochemical having a melting point of at least about 25° C. and a molecular weight of about 500 to 2500, the fluorochemical being a fluorochemical piperazine, oxazolidinone or perfluorinated alkane having from 15 to 50 carbon atoms. U.S. Pat. No. 5,300,587 (Macia et al.) describes oil-repellent polymeric compositions made by blending a perfluoropolyether and a thermoplastic polymer. U.S. Pat. No. 5,336,717 (Rolando et al.) discloses fluorochemical graft copolymers derived from reacting monomers having terminal olefinic bonds with fluorochemical olefins having fluoroaliphatic groups and polymerizable double bonds.

International Published Application No. WO 98/15598 (Yamaguchi et al.) describes water- and oil-repellent resin compositions useful, e.g., for kitchenware and bathroom utensils, comprising thermoplastic or thermosetting resin and perfluoroalkylated polymer, such compositions exhibiting superior anti-fouling and mouldability. The perfluoroalkyl polymer can be a copolymer of a 5 to 18 carbon perfluoroalkyl group-containing (meth)acrylic ester and a hydrophilic group-bearing (meth)acrylic ester, with an optional copolymerizable comonomer which can be a $C_1$-$C_{25}$ (meth)acrylic acid alkyl ester, preferably a $C_8$-$C_{22}$ alkyl ester.

While these fluorochemical melt additives can in some circumstances impart satisfactory hydrophobicity and/or oleophobicity to thermoplastic resins they typically suffer from poor thermal stability above 300° C., a melt processing temperature often encountered in the industry, and they can also be prohibitively expensive, lending limitations to their commercial utility.

For many years nonwoven fibrous filter webs have been made from polypropylene using melt-blowing apparatus of the type described in Report No. 4364 of the Naval Research Laboratories, published May 25, 1954, entitled "Manufacture of Super Fine Organic Fibers" by Van Wente et al. Such melt-blown microfiber webs continue to be in widespread use for filtering particulate contaminants, e.g., as face masks and as water filters, and for other purposes, e.g., to remove oil from water.

Fibrous filters for removing particulate contaminants from the air are also made from fibrillated polypropylene films. Electret filtration enhancement can be provided by electrostatically charging the film before it is fibrillated. Common polymers such as polyesters, polycarbonates, etc. can be treated to produce highly charged electrets but these charges are usually short-lived especially under humid conditions. The electret structures may be films or sheets which find applications as the electrostatic element in electro-acoustic devices such as microphones, headphones and speakers and in dust particle control, high voltage electrostatic generators, electrostatic recorders and other applications.

SUMMARY

This disclosure provides a partially fluorinated sulfonamide compounds of the formula:

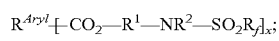

$$R^{Aryl}+CO_2-R^1-NR^2-SO_2R_f]_x; \qquad I$$

wherein
$R^{Aryl}$ is an aryl group;
$R^1$ is a linear or branched $C_2$-$C_{40}$ hydrocarbyl (both alkyl or aryl) group;
$R^2$ is a $C_1$-$C_4$ alkyl;
$R_f$ is a perfluorinated group of having an average of 3 to 5 carbon atoms;
and
subscript x is 1 to 3.

It has been reported that certain perfluorooctyl-containing compounds ($C_8F_{17}$—) may tend to bio-accumulate in living organisms; this tendency has been cited as a potential concern regarding some fluorochemical compositions. For example, see U.S. Pat. No. 5,688,884 (Baker et al.). As a result, there is a desire for fluorine-containing compositions effective in providing desired functional properties, e.g., water- and oil-repellency, surfactant properties, etc. while eliminating more effectively from biological systems. However, it has also been asserted that only perfluoroalkyl groups of the formula $F(CF_2)_n$— have six or greater carbons have the self-alignment capability to achieve useful performance, while shorter chains, e.g. $C_4F_9$— lack the self-alignment necessary for good performance. See Phillips and Dettree, J.Col and Interface Sci., vol. 56(2), August 1976.

Therefore it remains a challenge to provide shorter chain perfluoroalkyl compositions that are less bioaccumulative, while maintain the requisite performance.

This invention further provides a polymer composition comprising the partially fluorinated compounds of Formula I and a thermoplastic or thermoset polymer. A polymer composition of this invention can be melted or shaped, for example by extrusion or molding, to produce shaped articles, such as fibers, films and molded articles whose surfaces exhibit excellent oil- and water repellency. The repellent polymer composition is especially useful in the preparation of nonwoven fabrics used in medical gowns and drapes, where repellency to bodily fluids is mandated. Films made from repellent polymer compositions of this invention are useful, for example, for moisture and/or grease-resistant packaging, release liners, and multilayer constructions.

In another aspect, the present invention provides oily mist resistant electret filter media comprising polypropylene electret fibers made from repellent polymer compositions of this invention, wherein the fluorinated compound has a melting temperature of at least 25° C. Preferably the fibers may be in the form of meltblown microfibers.

In another aspect, the present invention provides a method for filtering particulate material from air containing oily aerosol particles comprising passing said air through electret filter media made from repellent polymer compositions of this invention. The electret filter media of the present invention have improved electret filtration enhancement and sustain that enhancement upon exposure to oily aerosols. Furthermore, the electret filter media of the present invention maintain functional filtration enhancing charge levels under accelerated aging conditions.

Fibrous polypropylene electret filters that are currently available, some made from melt-blown polypropylene microfibers and others from fibrillated polypropylene film, can show thermally stable electret filtration enhancement. Unfortunately, fibrous electret filters made of polypropylene, whether melt-blown microfibers or fibrillated film, tend to lose their electret enhanced filtration efficiency faster than desired for some purposes when exposed to oily aerosols. There is a need to improve the long-term efficiency of air filters in the presence of aerosol oils, especially in respirators.

The novel fibrous electret filter media of the present invention are especially useful as an air filter element of a respirator such as a face mask or for such purposes as heating, ventilation, and air-conditioning. In respirator uses, the novel electret filter media may be in the form of molded or folded half-face masks, replaceable cartridges or canisters, or prefilters. In such uses, an air filter element of the invention is surprisingly effective for removing oily aerosols such as are present in cigarette smoke or in fumes from combustion engines. When used as an air filter media, such as in a respirator, the electret filter media has surprisingly better filtration performance than does a comparable electret filter media made of 100% polypropylene fibers.

As used herein:

"Alkyl" means a linear or branched, cyclic or acylic, saturated or unsaturated monovalent hydrocarbon.

"Alkylene" means a linear or branched cyclic or acylic, saturated or unsaturated, polyvalent hydrocarbon.

"Alkenyl" means a linear or branched unsaturated hydrocarbon.

"Aryl" means a monovalent aromatic, such as phenyl, naphthyl and the like.

"Arylene" means a polyvalent, aromatic, such as phenylene, naphthalene, and the like.

"Aralkylene" means a group defined above with an aryl group attached to the alkylene, e.g., benzyl, 1-naphthylethyl, and the like.

"Hydrocarbyl" is inclusive of hydrocarbyl alkyl, alkylene and aryl groups of all indicated valent states. Unless otherwise indicated, the non-polymeric hydrocarbyl groups typically contain from 1 to 40 carbon atoms.

DETAILED DESCRIPTION

This disclosure provides fluorochemical sulfonamide compounds of the formula:

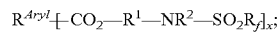  I wherein
$R^{Aryl}$ is an aryl group
$R^1$ is a linear or branched $C_2$-$C_{40}$ hydrocarbyl group;
$R^2$ is a $C_1$-$C_4$ alkyl;
$R_f$ is a perfluorinated group of having an average of 3 to 5 carbon atoms;
and subscript x is 1 to 3.

This disclosure provides fluorochemical compositions comprising a thermoplastic or thermoset polymer and at least one fluorinated sulfonamide compounds of Formula I.

In some preferred embodiments, the present fluorinated sulfonamide compounds and compositions thereof provide the necessary performance even with the shorter $C_3$-$C_5$ perfluoroalkyl groups. Furthermore, the short chain perfluorocarboxylic acids (the presumed intermediate degradation products) are less toxic and less bioaccumulative than the longer chain ($C_8$) homologues. For these reasons, the $R_f$ groups are selected from $C_3$-$C_5$ perfluoroalkyl groups. In preferred embodiments, $R_f$ is selected contains at least 95% linear $C_3$-$C_5$ groups and less than 5% of other perfluoroalkyl groups.

$R^{Aryl}$ is an aryl group having a valence of 1-3, including phenyl, napthyl, anthracenyl, phenanthanenyl, benzonapthanenyl, and fluorenyl. The aryl groups may be further substituted with one or more alkyl groups, i.e. an alkarylene group. Preferred $R^{Aryl}$ groups include ortho- or meta-substituted phenyl.

$R^1$ is selected as a non-fluorinated hydrocarbyl moiety, $R^1$ in may be a linear or branched chain, saturated or unsaturated, cyclic or acyclic (or any combination thereof) alkyl or alkylene group having from 1 to 40 carbon atoms and 1 to 20 in-chain oxygen atoms. Alternatively R may contain aryl or arylene groups. The range of structures contemplated for the organic moiety R will be better understood with reference to the compounds suitable for use in steps of the Reaction Schemes described in detail below.

In some embodiments $R^1$ is a linear or branched alkylene group of 1 to 40, preferably 2 to 30, and most preferably 2 to 10 carbon atoms of the formula-$C_nH_{2n}$—, where n is 1 to 40, preferably 2 to 30, and most preferably 2 to 20. The alkyl or alkylene groups may be further substituted by one or more aryl groups, i.e. an aralkylene. In other embodiments, R1 is a trivalent alkylene of the formula —$C_nH_{2n-1}$— where n is 1 to 40, preferably 2 to 30, and most preferably 2 to 20. In such embodiments, R1 may be designated as $R^{Alkyl}$ in Formula II.

The fluoroaliphatic sulfonamide compounds can be prepared using known organic reactions, such as those disclosed in U.S. Pat. No. 5,451,622 (Boardman et al, incorporated herein by reference. A preferred method of preparation is by the reaction of fluoroaliphatic radical-containing sulfonamide alkanol with and aryl acyl halide or ester.

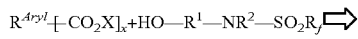  I where
$R^{Aryl}$ is an aryl group;
$R^1$ is a linear or branched $C_2$-$C_{40}$ hydrocarbyl group;
$R^2$ is a $C_1$-$C_4$ alkyl;
$R_f$ is a perfluorinated group of having an average of 3 to 5 carbon atoms;
X is a leaving groups including halide, alkoxy, tosyl and ester;
and subscript x is 1 to 3.

Alternatively, the aryl acyl halide (or ester) is first reacted with an alkanol of the formula HO—$R^1$—X', where X' is a leaving group, followed by reactions with a sulfonamide.

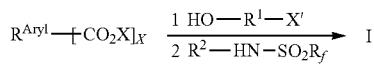 I where
$R^{Aryl}$ is an aryl group;
$R^1$ is a linear or branched $C_2$-$C_{40}$ hydrocarbyl group;
$R^2$ is a $C_1$-$C_4$ alkyl;
$R_f$ is a perfluorinated group of having an average of 3 to 5 carbon atoms;
X and X' are independently leaving groups including halide, alkoxy, tosyl and ester; and subscript x is 1 to 3.

As it is preferred that the $R_f$ groups are linear perfluoroalkyl groups, and have less than 5 mole % non-linear isomers, the perfluroalkylsulfonyl halide starting material is desirable prepared by electrochemical fluorination (ECF) of a linear $C_3$-$C_5$ sulfonyl fluoride, preferably a linear $C_4$ sulfonyl fluoride. With longer chain sulfonyl fluorides, the electrochemical fluorination yields a complex mixture of linear and branched isomers, as well as higher and lower homologues. ECF of linear $C_3$-$C_5$ alkyl sulfonyl fluorides yields predominately linear products with minor amounts of homologues.

The present invention provides a synthetic organic polymer composition comprising the one or more of the fluorinated oligomers of Formula I and a thermoplastic or thermoset organic polymer. The compounds of Formula I are useful as polymer melt additives to impart desirable low surface energy properties to the thermoplastic or thermoset polymer.

Useful polymers include both thermoplastic and thermoset polymers and include polyamides, e.g., nylon-6 and nylon-66, polyesters, e.g., polyethylene terephthalate, polyurethanes, epoxides, epoxy resins, (meth)acrylates, polystyrenes, silicones and polyolefins, e.g., polyethylene and polypropylene. Thermoplastic polymers such as polyolefins are preferred. The resultant articles, due to the presence of the fluorochemical additive, have improved oil- and water-repellency, low surface energy and a resistance to soiling.

Shaped articles (e.g., fibers, films and molded or extruded articles) of this invention can be made, e.g., by blending or otherwise uniformly mixing the alkylated fluorochemical oligomer and the polymer, for example by intimately mixing the oligomer with pelletized or powdered polymer, and melt extruding the mixture into shaped articles such as pellets, fibers, or films by known methods. The additive can be mixed per se with the polymer or can be mixed with the polymer in the form of a "masterbatch" (concentrate) of the additive in the polymer. Masterbatches typically contain from about 10% to about 25% by weight of the fluorochemical additive. Also, an organic solution of the additive may be mixed with the powdered or pelletized polymer, the mixture dried to remove solvent, then melted and extruded into the desired shaped article. Alternatively, molten additive (as a compound(s) or masterbatch) can be injected into a molten polymer stream to form a blend just prior to extrusion into the desired shaped article.

When using thermoset resins, such as epoxy resins, urethanes and acrylates, the fluorochemical oligomer may be mixed with the resin and cured by application of heat. Preferably such thermoset resins may be processed by reactive extrusion techniques such as are taught in U.S. Pat. No. 4,619,976 (Kotnour) and U.S. Pat. No. 4,843,134 (Kotnour).

The thermoplastic composition containing the compounds of Formula I may be used to provide oil and water repellency to fibers. The fluorochemical additives are melt processible, i.e., suffer substantially no degradation under the melt processing conditions used to form the fibers.

The amount of fluorochemical compound in the composition is that amount sufficient to produce a shaped article having a surface with the desired properties of oil and water repellency and/or soiling resistance. Preferably, the amount of fluorochemical compound will be that amount which provides from about 100 to 10,000 ppm fluorine, more preferably 200 to 5000 ppm, most preferably 400 to 3000 ppm fluorine, based on the weight of the shaped article.

After melt extrusion of a fiber, film or extruded article, an annealing step may be carried out to enhance oil and water repellency. Annealing apparently allows the fluorochemical additive to migrate to the surface of the thermoplastic polymer with a resultant increase in repellency properties, reduced surface activity, improved solvent resistance and improved release properties. The fiber or film is annealed for at a temperature and for a time sufficient to increase the amount of fluorochemical additive at the surface. Effective time and temperature will bear an inverse relationship to one another and a wide variety of conditions will be suitable. Using polypropylene, for example, the annealing process can be conducted below the melt temperature at about 50° to 120° C. for a period of about 30 seconds to 10 minutes. Annealing may also be effected by contact with heated rolls, such as embossing rolls, at 50° C. to 160° C. for periods of about 1 to 30 seconds. In some cases, the presence of moisture during annealing, e.g., by using an autoclave to anneal, can improve the effectiveness of the fluorochemical additive. The annealing method may also serve to reduce the amount of additive necessary by maximizing fluorine content at the surface of the polymer.

In addition to their use in modifying the properties of fibers, the polymer composition of the invention is also useful in preparing blown microfibers for non-woven fabrics having low surface energy, oil and water repellency and/or soiling resistance. The resin, such as polypropylene, used to form the melt blown microfibers should be substantially free from materials such as antistatic agents which could increase the electrical conductivity or otherwise interfere with the ability of the fibers to accept and hold electrostatic charges. When the fluorochemical compounds of the invention are used as additives to melt blown microfibers, the additive is preferably present in amounts of about 0.2 to 10 weight percent, more preferably from 0.5 to 5 weight percent and most preferably 0.5 to 2 weight percent.

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion.

The non-woven webs of fibers of thermoplastic olefinic polymer for use in this invention include non-woven webs manufactured by any of the commonly known processes for producing non-woven webs. For example, the fibrous nonwoven web can be made by spunbonding techniques or melt-blowing techniques or combinations of the two. Spunbonded fibers are typically small diameter fibers which are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Any of the non-woven webs may be made from a single type of fiber or two or more fibers which differ in the type of thermoplastic olefinic polymer and/or thickness. Alternatively, sheath-core fibers can be extruded, containing different polymer compositions in each layer or containing the same polymer composition in each layer but employing the more expensive fluorochemical component in the outer sheath layer.

The melt blown polypropylene microfibers useful in the present invention can be prepared as described in Van Wente, A., "Superfine Thermoplastic Fibers," Industrial Engineering Chemistry, vol. 48, pp. 1342-1346 (1956) and in Report No. 4364 of the Naval Research Laboratories, published May 25, 1954, entitled "Manufacture of Super Fine Organic Fibers" by Van Wente et al. or from microfiber webs containing particulate matter such as those disclosed, for example, in U.S. Pat. No. 3,971,373 (Braun), U.S. Pat. No. 4,100,324 (Anderson) and U.S. Pat. No. 4,429,001 (Kolpin et al.). Multilayer constructions of nonwoven fabrics enjoy wide industrial and commercial utility and include uses such as fabrics for medical gowns and drapes. The nature of the constituent layers of such multilayer constructions can be varied according to the desired end use characteristics, and can comprise two of more layers of meltblown and spun-bond webs in may useful combinations such as described in U.S. Pat. Nos. 5,145,727 and 5,149,576. The filtering efficiency of a melt-blown microfiber web can be improved by a factor of two or more when the melt-blown fibers are bombarded as they issue from the orifices with electrically charged particles such as electrons or ions, thus making the fibrous web an electret. Similarly, the web can be made an electret by exposure to a corona after it is collected. Melt-blown polypropylene microfibers are especially useful, while other polymers may also be used such as polycarbonates and polyhalocarbons that may be melt-blown and have appropriate volume-resistivities under expected environmental conditions.

Any of a wide variety of constructions, especially multilayer constructions such as SMS (spunbond/meltblown/spunbond) constructions, may be made from the above-described fibers and fabrics, and such constructions will find utility in any application where some level of hydrophobicity, oleophobicity (or other fluid repellency, such as to bodily fluids) is required. The fibers prepared from the synthetic organic polymer composition of the invention may be used in woven and nonwoven medical fabrics (such as drapes, gowns and masks), industrial apparel, outdoor fabrics (such as umbrellas, awning, tents, etc), raincoats and other outdoor apparel, as well as home furnishings such as table linens and shower curtains, and in myriad other related uses.

Preferably, the filter media is annealed, i.e., heated for a sufficient time at a sufficient temperature to cause the fluorochemical additive to bloom to the surface of the fibers. Generally, about 1 to 10 minutes at about 140 deg. C. is sufficient although shorter times may be used at higher temperatures and longer times may be required at lower temperatures.

Blown microfibers for fibrous electret filters of the invention typically have an effective fiber diameter of from about 5 to 30 micrometers, preferably from about 7 to 10 micrometers, as calculated according to the method set forth in Davies, C. N., "The Separation of Airborne Dust and Particles," Institution of Mechanical Engineers, London, Proceedings 1B, 1952.

The electret filter media of the present invention preferably has a basis weight in the range of about 10 to 500 g/m$^2$, more preferably about 10 to 100 g/m$^2$. In making meltblown microfiber webs, the basis weight can be controlled, for example, by changing either the collector speed or the die throughput. The thickness of the filter media is preferably about 0.25 to 20 mm, more preferably about 0.5 to 2 mm. The electret filter media and the polypropylene resin from which it is produced should not be subjected to any unnecessary treatment which might increase its electrical conductivity, e.g., exposure to gamma rays, ultraviolet irradiation, pyrolysis, oxidation, etc.

The melt-blown microfibers or fibrillated fibers of the electret filters of the invention can be electrostatically charged by a process described in U.S. Pat. Nos. Re. 30,782 (van Turnhout) or Re. 31,285 (van Turnhout) or by other conventional methods for charging or polarizing electrets, e.g., by a process of U.S. Pat. No. 4,375,718 (Wadsworth et al.); U.S. Pat. No. 4,588,537 (Klasse et al.); or U.S. Pat. No. 4,592,815 (Nakao). In general, the charging process involves subjecting the material to corona discharge or pulsed high voltage.

Films prepared from the composition of this invention can be made which are useful, for example, for grease-resistant packaging, release liners and microporous film applications. These films can be used to make multi-layer constructions in which one, more than one, or all layers contain the fluorochemical additive.

This invention is illustrated by, but is not intended to be limited to, the following examples. Unless otherwise specified, all percentages shown in the examples and test methods, which follow, are percentages by weight.

EXAMPLES

Materials

Unless otherwise indicated all chemicals were obtained or are commonly available from chemical companies such as Sigma-Aldridge Chemical Company, St. Louis, Mo. C18 Diester ($C_4F_9SO_2N(CH_3)CH_2CH_2OOC(CH_2)_{16}COO\ CH_2CH_2(CH_3)NSO_2C_4F_9$), was prepared by following the process described in F-4 of U.S. Pat. No. 7,396,866 B2.

Methods

Method for Water Repellency Test

To run the Water Repellency Test, film samples prepared according to the Examples and Comparative Examples described below were placed on a flat, horizontal surface. Five small drops of water or a water/isopropyl alcohol (IPA) mixture were gently placed at points at least two inches (about 5 cm) apart on the film samples. If, after observing for ten seconds at a 45° angle, four of the five drops were visible as a sphere or a hemisphere, the film sample was deemed to pass the test. The reported water repellency rating corresponds to the highest numbered water or water/IPA mixture for which the film sample passed the above described test. It is desirable to have a water repellency rating of at least 4, preferably at least 6. The water repellency ratings and the corresponding water/IPA mixtures are shown in Table 1, below:

TABLE 1

| Water Repellence Rating | Water/IPA Blend (% volume) |
|---|---|
| 0 | 100/0 |
| 1 | 90/10 |
| 2 | 80/20 |
| 3 | 70/30 |
| 4 | 60/40 |
| 5 | 50/50 |
| 6 | 40/60 |
| 7 | 30/70 |
| 8 | 20/80 |
| 9 | 10/90 |
| 10 | 0/100 |

Preparative Example 1 (PE1)

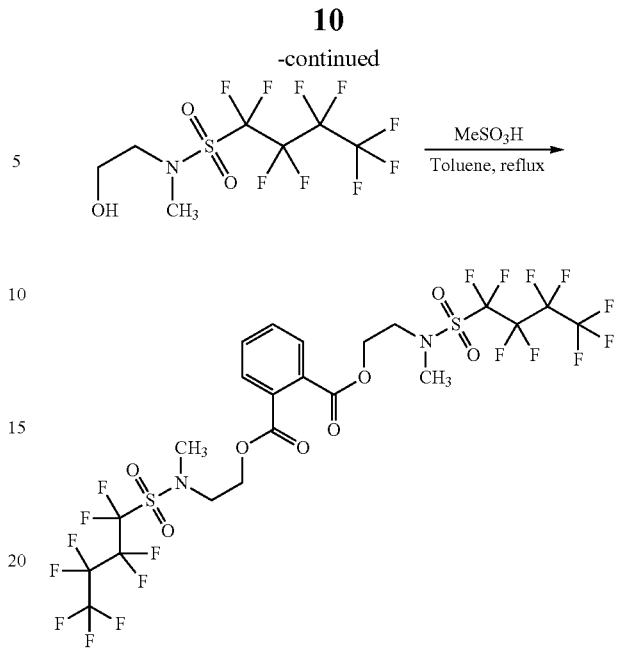

1,1,2,2,3,3,4,4,4-nonafluoro-N-(2-hydroxyethyl)-N-methyl-butane-1-sulfonamide (249 g, 697.11 mmol), methanesulfonic acid (1.73 mL, 26.1 mmol), isobenzofuran-1,3-dione (51.5 g, 348 mmol) and toluene (174 mL, 1630 mmol) were added to a 500 mL round bottom flask equipped with a magnetic stir bar and reflux condenser. The reaction mixture was stirred at 110° C. for 18 h. Triethylamine (3.67 mL, 26.1 mmol) was then added to the resulting pale yellow solution and the reaction mixture was allowed to cool to room temperature. The resulting precipitate was collected via filtration, washed with toluene and dried under vacuum to afford bis[2-[methyl(1,1,2,2,3,3,4,4,4-nonafluorobutylsulfonyl)amino]ethyl] benzene-1,2-dicarboxylate (273 g, 323.3 mmol, 93.0% Yield) as a white solid. The identity of the material was confirmed by LC/MS and NMR techniques.

Preparative Example 2 (PE2)

-continued

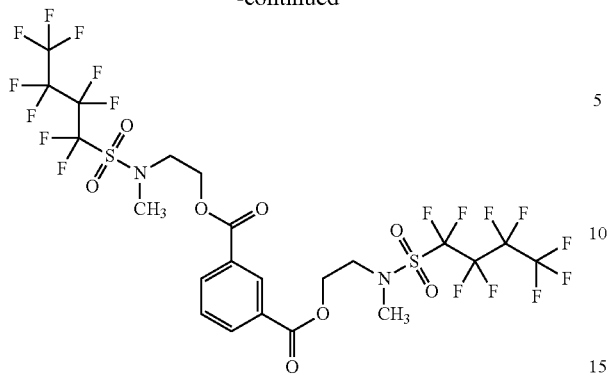

1,1,2,2,3,3,4,4,4-nonafluoro-N-(2-hydroxyethyl)-N-methyl-butane-1-sulfonamide (2.01 equiv., 566 mmol), triethylamine (2.2 equiv., 620 mmol) and toluene (0.5 M, 5280 mmol) were added to a 1 L 3-neck flask equipped with mechanical stirrer, reflux condenser and addition funnel containing benzene-1,3-dicarbonyl chloride (57.2 g, 282 mmol) dissolved in a mixture of toluene and dichloromethane. Under positive pressure of nitrogen, the dissolved alcohol was added to the stirring reaction mixture. An exotherm was observed and a white precipitate began to form. Upon completion of addition, the reaction mixture was allowed to stir at room temperature for 18 h at which point water (300 mL) was added. The mixture was allowed to stir for 5 minutes and the resulting white solid was collected via filtration and then washed sequentially with dichloromethane (300 mL, 3×) and water (300 mL, 3×). The resulting white powder was dried via azeotropic distillation of toluene to afford bis[2-[methyl(1,1,2,2,3,3,4,4,4-nonafluorobutyl-sulfonyl)amino]ethyl] benzene-1,3-dicarboxylate (219 g, 259.3 mmol, 92.0% Yield) as a white solid. The identity of the material was confirmed by LC/MS and NMR techniques.

Preparative Example 3 (PE3)

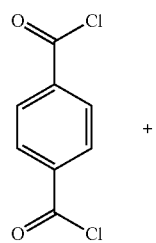
+

-continued

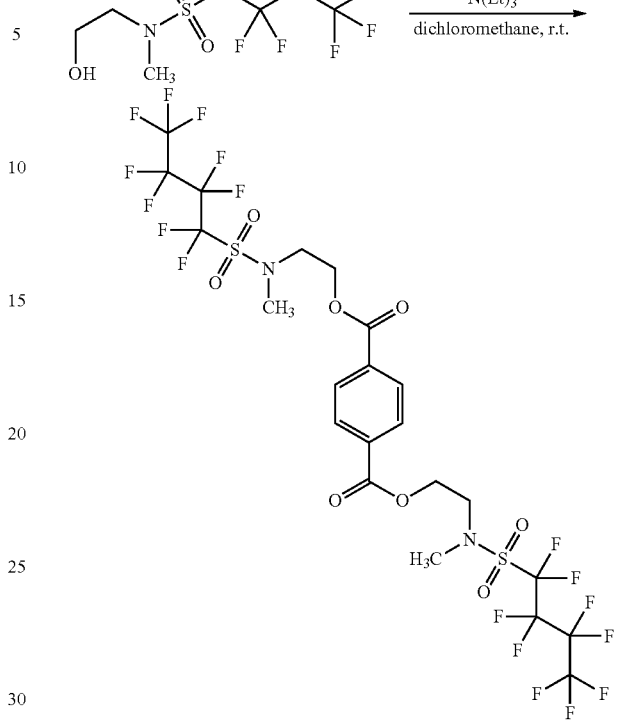

1,1,2,2,3,3,4,4,4-nonafluoro-N-(2-hydroxyethyl)-N-methyl-butane-1-sulfonamide (176.82 g, 495.03 mmol), triethylamine (54.827 g, 541.82 mmol) and dichloromethane (500 mL, 7800 mmol) were added to a 1 L 3-neck flask equipped with mechanical stirrer, reflux condenser and addition funnel containing benzene-1,4-dicarbonyl chloride (50 g, 246.28 mmol) dissolved in dichloromethane. Under positive pressure of nitrogen, the dissolved alcohol was added to the stirring reaction mixture. An exotherm was observed and a white precipitate began to form. Upon completion of addition, the reaction mixture was allowed to stir at room temperature for 18 h at which point water (300 mL) was added. The mixture was allowed to stir for 5 minutes and the resulting white solid was collected via filtration and then washed sequentially with dichloromethane (300 mL, 3×) and water (300 mL, 3×). The resulting white powder was dried via azeotropic distillation of toluene to afford bis[2-[methyl(1,1,2,2,3,3,4,4,4-nonafluorobutyl-sulfonyl)amino]ethyl]benzene-1,4-dicarboxylate (202 g, 239.2 mmol, 97.12% Yield) as a white solid. The identity of the material was confirmed by LC/MS and NMR techniques.

Preparative Example 4 (PE4)

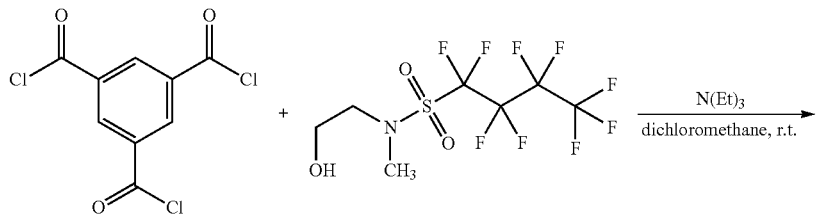

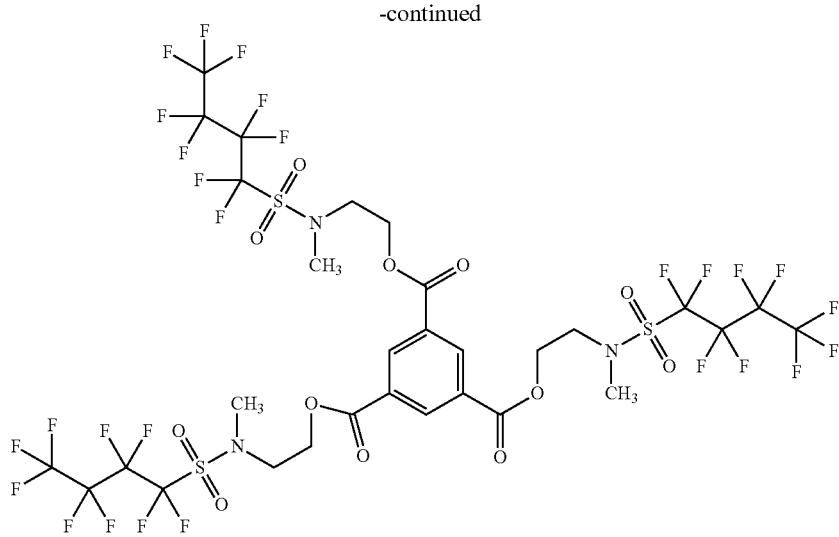

1,1,2,2,3,3,4,4,4-nonafluoro-N-(2-hydroxyethyl)-N-methyl-butane-1-sulfonamide (4.05 g, 11.3 mmol), triethylamine (1.73 mL, 12.4 mmol), and dichloromethane (7.5 mL, 0.5 M, 117.5 mmol) were added to a 20 mL vial equipped with a magnetic stirrer. Benzene-1,3,5-tricarbonyl chloride (1.0 g, 3.7668 mmol) dissolved in dichloromethane, was added slowly to the stirring reaction mixture. An exotherm was observed and a white precipitate began to form. Upon completion of addition of benzene-1,3,5-tricarbonyl chloride, the reaction mixture was allowed to stir at room temperature for 18 h at which point the reaction mixture was poured into a beaker containing water (300 mL). The mixture was allowed to stir for 5 minutes and the resulting white solid was collected via filtration and then washed sequentially with dichloromethane (50 mL, 3×) and water (50 mL, 3×). The resulting white powder was dried under high vacuum and heat for 72 h to afford tris[2-[methyl(1,1,2,2,3,3,4,4,4-nonafluorobutylsulfonyl)amino]ethyl] benzene-1,3,5-tricarboxylate (3.0 g, 2.4436 mmol, 65% Yield) as a white solid. The identity of the material was confirmed by LC/MS and NMR techniques.

Examples 1-3 (EX1-EX3) and Comparative Examples 4-5(CE4-CE5)

To prepare EX1-EX3, first, a 4 weight % solution of 95:5 polyurethane binder:additive in MEK was prepared. The additives used in EX1-EX3 were prepared as described above in PE1-PE3, respectively. Then EX1-EX3 samples were prepared by coating the resulting coating solutions onto glass slides, drying and annealing at either 175° C. or 110° C.

CE4 was prepared in the same manner as EX1-EX3 described above except that $C_4F_9SO_2N(CH_3)CH_2CH_2OOC(CH_2)_{16}COOCH_2CH_2(CH_3)NSO_2C_4F_9$ was the fluorochemical additive.

CE5 was prepared in the same manner as EX1-EX3 described above, except that no fluorochemical additive was present.

The resulting EX1-EX3 and CE4-CE5 film samples were tested for their water repellency using the test method described above. The results are reported in Table 2, below.

TABLE 2

| Example | Additive | Cure Temperature (° C.) | Water Repellency Rating |
|---|---|---|---|
| EX1 | PE1 | 175 | 4 |
| EX2 | PE2 | 175 | 9 |
| EX3 | PE3 | 175 | 4 |
| CE4 | C18 Diester | 110 | 10 |
| CE5 | None | 175 | 0 |

What is claimed is:

1. A composition comprising a thermoplastic polymer and an additive of the formula:

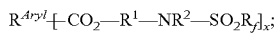

wherein
$R^{Aryl}$ is an aryl group;
$R^1$ is a linear or branched $C_2$-$C_{40}$ hydrocarbyl group;
$R^2$ is a $C_1$-$C_4$ alkyl;
$R_f$ is a perfluorinated group of having an average of 3 to 5 carbon atoms;
and
subscript x is 1 to 3.

2. The composition of claim 1 wherein the additive contains at least 95% linear perfluorobutyl groups.

3. The composition of claim 1 wherein the additive contains less than 5% of other perfluoroalkyl groups.

4. The composition of claim 1 wherein said thermoplastic polymer is selected from the group consisting of polyamides, polyesters, polyurethanes, epoxides, epoxy resins, (meth)acrylates, polystyrenes, silicones and polyolefins.

5. The composition of claim 1 wherein said additive comprises from 0.1 to 5 weight percent of said composition.

6. The composition of claim 1 wherein $R^1$ is a $C_2$-$C_{40}$ alkylene.

7. The composition of claim 1 wherein $R^1$ is a $C_2$-$C_{30}$ alkylene.

8. The composition of claim 1 wherein $R^{Aryl}$ is selected from phenyl, napthyl, anthracenyl, phenanthanenylbenzonapthanenyl, and fluorenyl.

9. The composition of claim 8 wherein the $R^{Aryl}$ is selected from ortho- or meta-substituted phenyl.

10. A shaped article comprising the composition of claim 1.

11. The shaped article of claim 10 selected from the group of films, sheets and fibers.

\* \* \* \* \*